(12) United States Patent
Mazzeo et al.

(10) Patent No.: US 9,470,661 B2
(45) Date of Patent: Oct. 18, 2016

(54) METHOD AND SYSTEM FOR STRUCTURAL INTEGRITY ASSESSMENT

(71) Applicant: Brigham Young University, Provo, UT (US)

(72) Inventors: Brian A. Mazzeo, Provo, UT (US); William S. Guthrie, Provo, UT (US); Anjali N. Patil, Orem, UT (US)

(73) Assignee: Brigham Young University, Provo, UT (US)

( * ) Notice: Subject to any disclaimer, the term of this patent is extended or adjusted under 35 U.S.C. 154(b) by 248 days.

(21) Appl. No.: 14/206,703

(22) Filed: Mar. 12, 2014

(65) Prior Publication Data

US 2014/0260527 A1 Sep. 18, 2014

Related U.S. Application Data

(60) Provisional application No. 61/778,348, filed on Mar. 12, 2013, provisional application No. 61/842,486, filed on Jul. 3, 2013.

(51) Int. Cl.
*G01N 3/00* (2006.01)
*G01N 3/08* (2006.01)
*G01N 29/04* (2006.01)
*G01N 29/14* (2006.01)
*G01N 29/38* (2006.01)
(Continued)

(52) U.S. Cl.
CPC ............ *G01N 29/045* (2013.01); *G01N 29/14* (2013.01); *G01N 29/38* (2013.01); *G01N 29/4472* (2013.01); *G01N 29/46* (2013.01); *G01N 2291/0232* (2013.01); *G01N 2291/044* (2013.01)

(58) Field of Classification Search
CPC ............ G01N 2203/0039; G01N 2203/0033; G01N 2291/0232; G01N 2291/0423; G01N 2291/044; G01N 29/14; G01N 29/045; G01N 29/032; G01N 33/383
USPC ......... 73/12.01, 12.04–12.14, 584, 587, 589, 73/594, 596, 597, 598, 609–617, 620–648
See application file for complete search history.

(56) References Cited

U.S. PATENT DOCUMENTS

| | | | |
|---|---|---|---|
| 4,696,191 A * | 9/1987 | Claytor | G01N 29/032 73/19.01 |
| 4,775,028 A | 10/1988 | de Heering | |
| 5,048,320 A * | 9/1991 | Mitsuhashi | G01M 7/08 73/12.09 |

(Continued)

FOREIGN PATENT DOCUMENTS

WO 2014/165163 A1 10/2014

OTHER PUBLICATIONS

International Search Report and Written Opinion received for PCT Patent Application No. PCT/US2014/024614, mailed on Jul. 22, 2014, 13 pages.

(Continued)

*Primary Examiner* — Lisa Caputo
*Assistant Examiner* — Jonathan Dunlap
(74) *Attorney, Agent, or Firm* — Brake Hughes Bellermann LLP

(57) ABSTRACT

The method includes dispensing an object at a portion of concrete, determining an impact time of the object on the portion of concrete, detecting at least one acoustic wave reflected from the portion of concrete, filtering the at least one acoustic wave, and identifying a defect in the portion of concrete based on the filtering.

19 Claims, 10 Drawing Sheets

(51) Int. Cl.
G01N 29/44 (2006.01)
G01N 29/46 (2006.01)

(56) References Cited

U.S. PATENT DOCUMENTS

| | | | | |
|---|---|---|---|---|
| 5,867,404 | A * | 2/1999 | Bryan | B61K 9/08 |
| | | | | 342/457 |
| 5,983,701 | A * | 11/1999 | Hassani | G01N 3/307 |
| | | | | 73/12.01 |
| 5,996,413 | A | 12/1999 | Iyer et al. | |
| 6,105,430 | A * | 8/2000 | Kepler | G01N 29/045 |
| | | | | 73/12.01 |
| 6,257,064 | B1 | 7/2001 | Duron | |
| 6,684,681 | B1 * | 2/2004 | Zombo | B06B 1/045 |
| | | | | 73/12.11 |
| 6,890,302 | B2 * | 5/2005 | Oravecz | G01S 7/52053 |
| | | | | 600/443 |
| 7,694,567 | B2 | 4/2010 | Haupt et al. | |
| 8,567,252 | B2 * | 10/2013 | Fisk | G01N 29/265 |
| | | | | 73/12.11 |
| 2004/0025593 | A1 | 2/2004 | Hashimoto et al. | |
| 2005/0199064 | A1 * | 9/2005 | Wen | G01H 1/00 |
| | | | | 73/584 |
| 2011/0259128 | A1 | 10/2011 | Ziehl et al. | |
| 2015/0033864 | A1 * | 2/2015 | Kumar | G01N 29/265 |
| | | | | 73/636 |

OTHER PUBLICATIONS

"Standard Practice for Measuring Delaminations in Concrete Bridge Decks by Sounding", ASTM International, Designation: D 4580-03, Sep. 2003, pp. 1-4.
"Standard Specification for Ready-Mixed Concrete", ASTM International, Designation: C 94/C 94M-04a, Sep. 2004, pp. 1-11.
Aggelis et al., "Evaluation of Grouting in Tunnel Lining Using Impact-Echo", Tunnelling and Underground Space Technology, vol. 23, Issue 6, Nov. 2008, pp. 629-637.
Algernon et al., "Signal Processing for Air-Coupled Impact-Echo using Microphone Arrays", 18th World Conference on Nondestructive Testing, Durban, South Africa, Apr. 16-20, 2012, 8 pages.
Bjurström et al., "Air-Coupled Detection of the S1-ZGV Lamb Mode in a Concrete Plate Based on Backward Wave Propagation", Review of Progress in Quantitative Nondestructive Evaluation: vol. 32, AIP Conference Proceedings, vol. 1511, 2013, pp. 1294-1300.
Carino, Nicholas J., "The Impact-Echo Method: An Overview", Reprinted from the Proceedings of the 2001 Structures Congress & Exposition, May 21-23, 2001, American Society of Civil Engineers, 2001, pp. 1-18.
Carino, Nicholas J., "Training: Often the Missing Link in Using NDT Methods", Construction and Building Materials, vol. 38, Jan. 2013, pp. 1316-1329.
Colla et al., "Influence of Source Frequency on Impact-Echo Data Quality for Testing Concrete Structures", NDT&E International, vol. 36, Issue 4, Jun. 2003, pp. 203-213.
Dai et al., "A Focused Electric Spark Source for Non-Contact Stress Wave Excitation in Solids", The Journal of the Acoustical Society of America, vol. 134, Issue 6, Nov. 6, 2013, 7 pages.
Dai et al., "Excitation of Rayleigh and Zero-Group-Velocity (ZGV) Lamb Waves Using Air-Borne N-Waves Focused by an Ellipsoidal Reflector", The Journal of Acoustical Society of America, vol. 19, Jun. 2-7, 2013, 5 pages.
Dai et al., "Use of Parabolic Reflector to Amplify In-Air Signals Generated During Impact-Echo Testing", Acoustical Society of America, vol. 130, Issue 4, Oct. 2011, 6 pages.
Federer et al., "Hail and Raindrop Size Distributions from a Swiss Multicell Storm", Journal of Applied Meteorology and Climatology, vol. 14, Feb. 1975, pp. 91-97.
Frugis et al., "Development of Warning Thresholds for One Inch or Greater Hail in the Albany New York County Warning Area", Eastern Region Technical Attachment, No. 2011-05, Aug. 2011, pp. 1-24.

Gibson et al., "Lamb Wave Basis for Impact-Echo Method Analysis", Journal of Engineering Mechanics, Apr. 2005, pp. 438-443.
Gucunski et al., "Impact Echo Data from Bridge Deck Testing Visualization and Interpretation", Transportation Research Record, Issue 2050, Accession No. 01090274, 2008, 2 pages. (Abstract Only).
Guegan et al., "Critical Impact Velocity for Ice Fragmentation", Journal of Mechanical Engineering Science, vol. 226, Issue 7, Nov. 15, 2011, pp. 1677-1682.
Guthrie, W. Spencer, "Effect of Initial Scarification and Overlay Treatment Timing on Chloride Concentrations in Concrete Bridge Decks", Transportation Research Board, 90th Annual Meeting, Paper No. 11-2728, Jan. 23-27, 2011, 23 pages.
Hema et al., "Construction and Condition Assessment of Concrete Bridge Decks and Decision Thresholds or Deck Rehabilitation and Replacement: State of the Practice", Transportation Research Board, 84th Annual Meeting, Jan. 9-13, 2005, 21 pages.
Higa et al., "Size Dependence of Restitution Coefficients of Ice in Relation to Collision Strength", ICARUS 133, Article No. IS985938, 1998, pp. 310-320.
Holland et al., "Air-Coupled Acoustic Imaging with Zero-Group-Velocity Lamb Modes", Applied Physics Letters, vol. 83, No. 13, Sep. 29, 2003, pp. 2704-2706.
Kee et al., "Nondestructive Bridge Deck Testing with Air-Coupled Impact-Echo and Infrared Thermography", Journal of Bridge Engineering, vol. 17, No. 6, Nov./Dec. 2012, pp. 928-939.
Knight et al., "Measurement and Interpretation of Hailstone Density and Terminal Velocity", Journal of the Atmospheric Sciences, vol. 40, Issue 6, Jun. 1983, pp. 1510-1516.
Koch et al., "Corrosion Cost and Preventive Strategies in the United States", CC Technologies Laboratories, Inc., FHWA-RD-01-156, Sep. 30, 2001, 110 pages.
Lin et al., "Use of the Normalized Impact-Echo Spectrum to Monitor the Setting Process of Mortar", NDT&E International, vol. 43, Issue 5, Jul. 2010, pp. 385-393.
Liu et al., "Spectral Tomography of Concrete Structures Based on Impact Echo Depth Spectra", NDT&E International, vol. 44, Issue 8, Dec. 2011, pp. 692-702.
Mazzeo et al., "Acoustic Impact-Echo Investigation of Concrete Delaminations Using Liquid Droplet Excitation", NDT&E International, vol. 51, Oct. 2012, pp. 41-44.
McLaskey et al., "Hertzian Impact: Experimental Study of the Force Pulse and Resulting Stress Waves", The Journal of the Acoustical Society of America, vol. 128, Issue 3, Sep. 2010, pp. 1087-1096.
Mitchell, David L., "Use of Mass- and Area-Dimensional Power Laws for Determining Precipitation Particle Terminal Velocities", Journal of the Atmospheric Sciences, vol. 53, No. 12, Jun. 15, 1996, pp. 1710-1723.
Oh, Tae Keun "Defect Characterization in Concrete Elements Using Vibration Analysis and Imaging", Submitted for the degree of Doctor of Philosophy in Civil Engineering in the Graduate College of the University of Illinois, May 22, 2012, 142 pages.
Ohtsu et al., "Quantitative Evaluation of SIBIE Procedure and Case Studies", Construction and Building Materials, vol. 48, Graduate School of Science and Technology, Kumamoto University, Japan, Nov. 2013, 7 pages.
Ryden et al., "Non-Contact Surface Wave Testing of Pavements Using a Rolling Microphone Array", Proceedings of 7th International Symposium on Nondestructive Testing in Civil Engineering, France, Jun. 30-Jul. 31, 2009, 6 pages.
Sansalone, Mary "Impact-Echo: The Complete Story", ACI Structural Journal, Technical paper, Title No. 94-871, Nov.-Dec. 1997, pp. 777-786.
Shin et al., "Cost Effective Air-Coupled Impact-Echo Sensing for Rapid Detection of Delamination Damage in Concrete Structures", Advances in Structural Engineering, vol. 15, No. 6, Multi Science Publishing, Jun. 2012, pp. 887-896. (Abstract only).
Song et al., "Bonding State Evaluation of Tunnel Shotcrete Applied onto Hard Rocks Using the Impact-Echo Method", NDT&E International, vol. 42, Issue 6, Sep. 2009, pp. 487-500.
Song et al., "Numerical Study on the Evaluation of Tunnel Shotcrete Using the Impact-Echo Method Coupled With Fourier Transform

(56) References Cited

OTHER PUBLICATIONS and Short-Time Fourier Transform", International Journal of Rock Mechanics and Mining Sciences, vol. 47, Issue 8, Dec. 2010, pp. 1274-1288.

Tsai et al., "Simulation and Experiments of Airborne Zero-Group-Velocity Lamb Waves in Concrete Plate", Journal of Nondestructive Evaluation, vol. 31, Issue 4, Dec. 2012, pp. 373-382.

Zhang et al., "An Automatic Impact-Based Delamination Detection System for Concrete Bridge Decks", NDT&E International, vol. 45, Issue 1, Jan. 2012, pp. 120-127.

Zhang et al., "Application of Noise Cancelling and Damage Detection Algorithms in NDE of Concrete Bridge Decks Using Impact Signals", Journal of Nondestructive Evaluation, vol. 30, Issue 4, Dec. 2011, pp. 259-272.

Zhang et al., "Ensemble Empirical Mode Decomposition of Impact-Echo Data for Testing Concrete Structures", NDT&E International, vol. 51, Oct. 2012, pp. 74-84.

Zhu et al., "Imaging Concrete Structures Using Air-Coupled Impact-Echo", Journal of Engineering Mechanics, vol. 133, Issue 6, Jun. 2007, pp. 628-640.

Zhu et al., "Leaky Rayleigh and Scholte Waves at the fluid-solid interface Subjected to Transient Point Loading", The Journal of the Acoustical Society of America, 116 (4), Pt. 1, Oct. 2004, pp. 2101-2110.

Zhu et al., "Non-contact NDT of Concrete Structures Using Air Coupled Sensors", NSEL Report Series, Report No. NSEL-010, May 2008, 119 pages.

\* cited by examiner

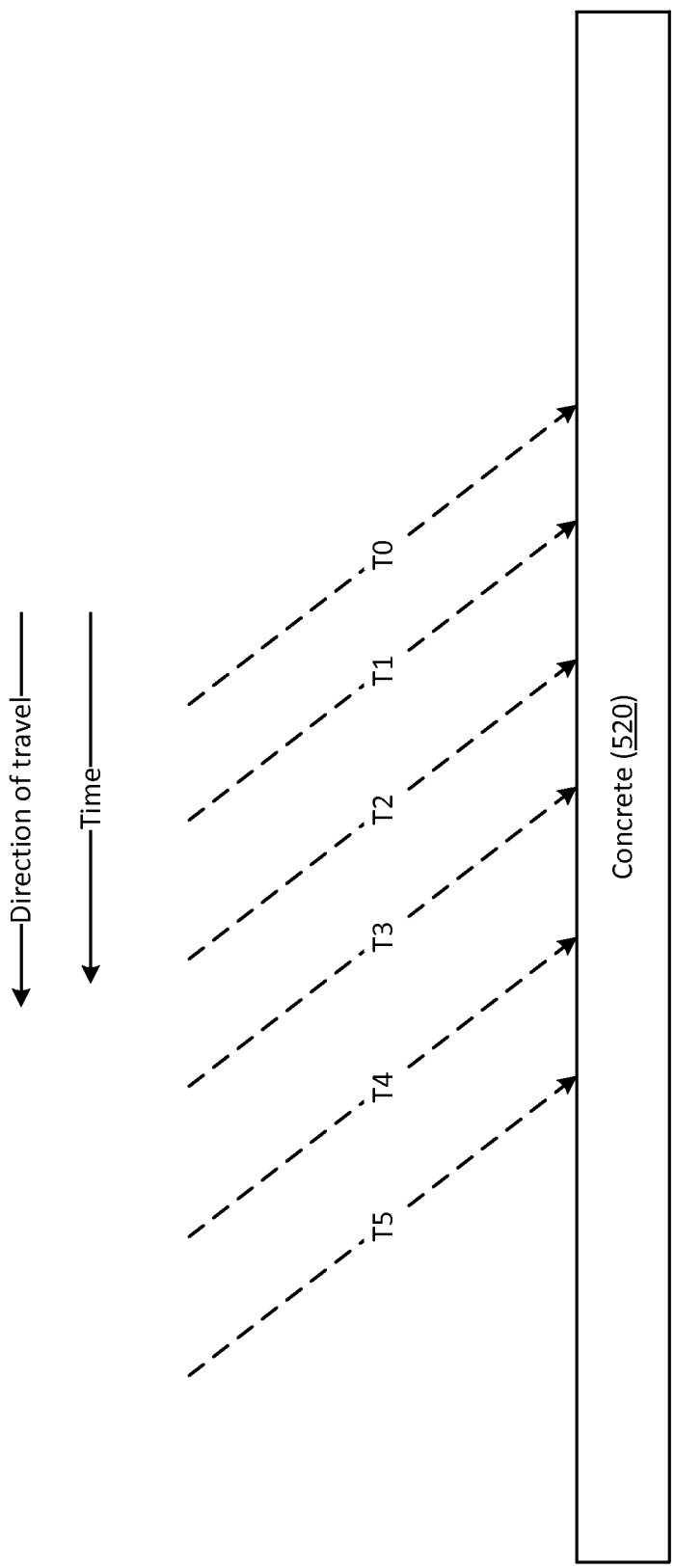

METHOD AND SYSTEM FOR STRUCTURAL INTEGRITY ASSESSMENT

This application claims the benefit of U.S. Provisional Patent Application 61/778,348 filed on Mar. 12, 2013 entitled "METHOD AND SYSTEM FOR STRUCTURAL INTEGRITY ASSESSMENT" and U.S. Provisional Patent Application 61/842,486 filed on Jul. 3, 2013 entitled "METHOD AND SYSTEM FOR STRUCTURAL INTEGRITY ASSESSMENT", the entire contents each of which are incorporated in their entirety herein by reference. This application is related to a co-pending Patent Cooperation Treaty (PCT) application entitled "METHOD AND SYSTEM FOR STRUCTURAL INTEGRITY ASSESSMENT", PCT/US2014/024614, the entire contents of which are incorporated herein by reference.

FIELD

Embodiments relate to detecting a defect in concrete.

BACKGROUND

Corrosion of reinforcing bars, or rebar, can be a serious deterioration mechanism in reinforced concrete affecting roadway and/or bridge service life and operation. As rust is two to six times larger in volume than the parent steel, the development of corrosion products leads to section loss in the steel and to cracking of the concrete, which is frequently manifest as a subsurface defect (e.g., delamination) of the concrete. Quantifying the percentage of concrete that is affected by a defect is an important aspect of assessing the structural health of the concrete.

Accurate detection of a defect can be difficult and inefficient using known systems and methods. Thus, a need exists for systems, methods, and apparatus to address the shortfalls of present technology and to provide other new and innovative features.

SUMMARY

One embodiment includes a method for detecting a defect in concrete. The method includes dispensing an object at a portion of concrete, determining an impact time of the object on the portion of concrete, detecting at least one acoustic wave reflected from the portion of concrete, filtering the at least one acoustic wave, and identifying a defect in the portion of concrete based on the filtering.

Another embodiment includes a system for detecting a defect in concrete. The system includes a dispenser configured to project an object toward a portion of concrete, a detector configured to detect at least one acoustic wave reflected from the portion of concrete in response to impact of the object, and an assessment device configured to filter the at least one acoustic wave and identify a defect based on the results of the filter.

Still another embodiment includes a computer readable medium. The computer readable medium includes code segments that, when executed by a processor, cause the processor to perform steps. The steps include processing a plurality of records from a datastore, the plurality of records including at least one measurement associated with an acoustic wave reflected from a portion of concrete upon impact of an object and information about the measurement, filtering the at least one measurement using at least one of a time domain filter and a frequency domain filter, and identifying a defect in the portion of concrete based on the filtered at least one measurement.

BRIEF DESCRIPTION OF THE DRAWINGS

Example embodiments will become more fully understood from the detailed description given herein below and the accompanying drawings, wherein like elements are represented by like reference numerals, which are given by way of illustration only and thus are not limiting of the example embodiments and wherein:

FIGS. 3-5A illustrate block diagrams of systems for detecting a defect in concrete according to at least one example embodiment.

FIG. 5B illustrates a time versus travel of object contact with concrete using the system for detecting a defect in concrete illustrated in FIG. 5A.

Figure 1:
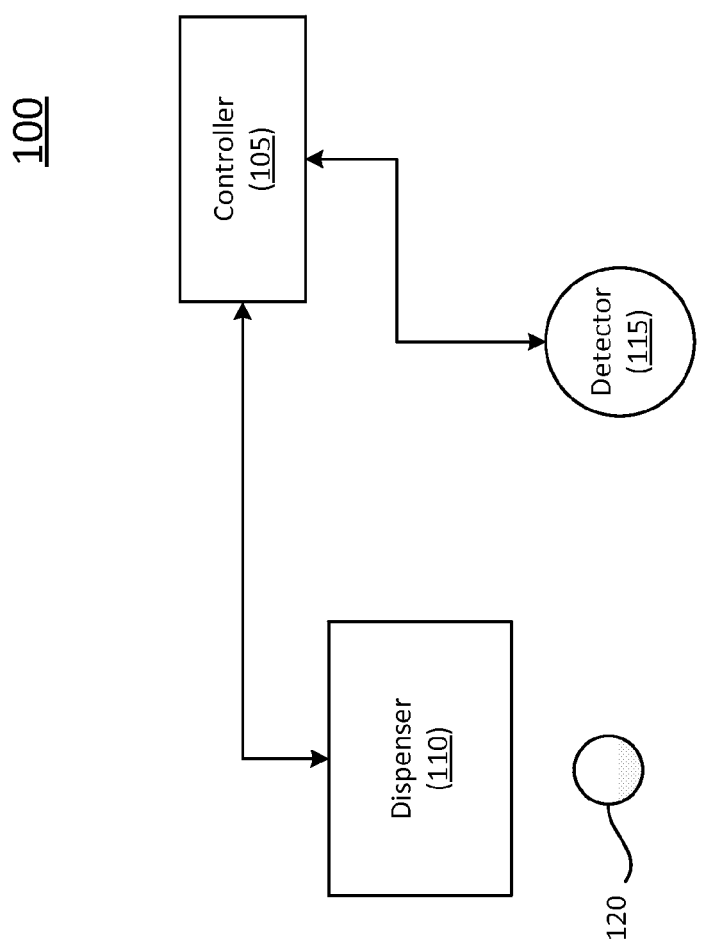
FIG. 1 illustrates a block diagram of a system for detecting a defect in concrete according to at least one example embodiment.

It should be noted that these Figures are intended to illustrate the general characteristics of methods, structure and/or materials utilized in certain example embodiments and to supplement the written description provided below. These drawings are not, however, to scale and may not precisely reflect the structural or performance characteristics of any given embodiment, and should not be interpreted as defining or limiting the range of values or properties encompassed by example embodiments. For example, the relative thicknesses and structural elements may be reduced or exaggerated for clarity. The use of similar or identical reference numbers in the various drawings is intended to indicate the presence of a similar or identical element or feature.

DETAILED DESCRIPTION

While example embodiments may include various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the claims. Like numbers refer to like elements throughout the description of the figures.

Although several non-destructive techniques have been investigated for this purpose, acoustic methods are the most widely used in the field. One example, chain dragging, consists of dragging a steel chain across a bridge deck surface and listening to changes in the acoustic response of the deck. While chain dragging has been used successfully for many years, chain dragging involves a degree of subjectivity, as even experienced operators may hear changes in the acoustic response of the deck differently, and its accuracy can be affected by operator fatigue. Another example is impact-echo testing, developed at the National Institute of Standards and Technology (NIST). The impact-echo testing technique involves exciting the concrete with an impulse-type loading and listening to the response. This method typically utilizes a rod to tap the concrete and a piezoelectric transducer to detect acoustic responses.

FIG. 1 illustrates a block diagram of a system for detecting a defect in concrete according to at least one example embodiment. As shown in FIG. 1, the system 100 includes a controller 105, a dispenser 110, a detector 115, and an object 120. The dispenser 110 may dispense the object 120 onto a portion of concrete (hereinafter concrete). The concrete may be a roadway and/or a portion of a roadway. For example, the concrete may be the surface, on which, for example, automobiles, bicycles, and so forth travel, of a bridge, a highway, walkway, and/or the like. The concrete may be a parking area, a warehouse floor, a water tank roof or other reinforced concrete element. The concrete may be a support. For example, the concrete may be a support for a bridge or a building. The concrete may be a concrete slab constructed for use in a test lab. The concrete may include metal shafts, rebar and/or other types of metallic and nonmetallic reinforcement. The concrete may be a vertical or horizontal surface of a building. The surface of the concrete may include a surface treatment. For example, a combination of epoxy and gravel, bitumen/asphalt and gravel, tile, paint, or some other surfacing applied to the concrete. The above are just examples to illustrate concrete, accordingly, example embodiments are not limited thereto.

The dispenser 110 may dispense (e.g., project, drop, launch, move) object 120. In other words, the dispenser 110 may use gravity to project or move object 120 toward the concrete. In cases where the dispenser 110 uses gravity, the dispenser can be referred to as a gravity-based dispenser. For example, a latched or trap door associated with the dispenser 110 may open to drop the object 120. The dispenser 110 may drop the object 120 from a fixed height (e.g., fixed in relation to the concrete). The dispenser 110 may launch object 120. In other words, the dispenser 110 may apply a force to project object 120 to the concrete or project the object 120 at a high velocity or a relatively high (e.g., as compared to gravity) velocity. In cases where the dispenser 110 launches objects, the dispenser 110 can be referred to as a launcher. For example, the dispenser 110 may use compressed gas and/or a spring to project (e.g., at a set speed or velocity) the object 120 toward the concrete. In other words the object 120 may be projected from the dispenser 110 as a compressed gas launch or a spring assisted launch.

The object 120 may be round, square, triangular, or the like. The object 120 may be environmentally neutral. In other words, the object 120 may dissipate (e.g., dissolve, biodegrade) into the environment without negative impact (e.g., relatively little negative impact, substantially no negative impact) on the environment surrounding the concrete. For example, the object 120 may be formed of ice. Accordingly, the object may melt and dissipate in the surrounding environment. For example, the object 120 may be formed of a biodegradable material (e.g., plastic) that breaks down in the surrounding environment. Environmentally neutral may also indicate that no (e.g., substantially no, relatively little) damage occurs to other elements (e.g., automobiles) in the surrounding environment. In other words, the object 120 may be formed of a material that may not damage a surface (e.g., paint or glass) of an automobile traveling on the concrete.

The detector 115 may be, or may include, a microphone. The detector 115 can also include a recorder. For example, the detector 115 can be a piezoelectric array microphone together with an acoustic sampling unit. The detector may also be a fiber optic microphone, a laser microphone, a silicon based microphone, a moving coil microphone, and the like. The recorder (or acoustic sampling unit) may be an element of the controller 105. The detector 115 may be close (or substantially close) to the concrete. For example, the detector 115 may be within 8, 12, 20, 25 cm of the concrete (e.g., of the impact point of the object 120 on the concrete) and directed towards the impact location. The detector 115 may be positioned based on an angle of impact of the object 120 as dispensed by the dispenser 110.

For example, in one implementation the angle of impact may affect what kind of surface wave modality directs energy towards the detector 115. Additionally, the time of arrival of the received acoustic response by the detector 115 may be affected by the distance of the detector 115 from the concrete. Accordingly, the distance from the detector 115 to the concrete surface should be small (or relatively small), for example 8, 12, 20, 25 cm, because a small distance may reduce the time between impact and response (especially for multiple shots at the concrete). Additionally, the amount of energy received lessens according to the surface area of the effective envelope surrounding the responding concrete.

Figure 2B:
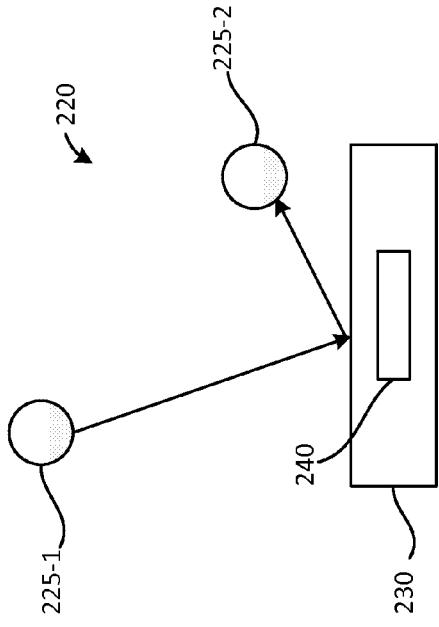
FIGS. 2A-2D illustrate generating acoustic waves when an object is dropped on concrete according to at least one example embodiment.
Figure 2D:
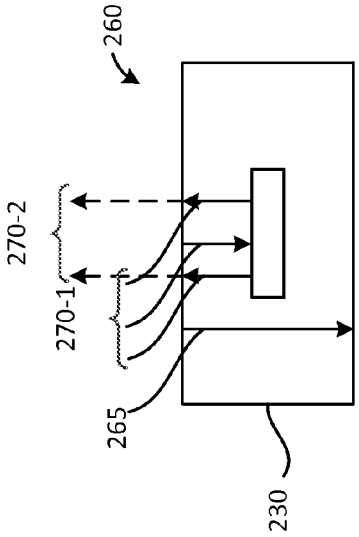
Figure 2A:
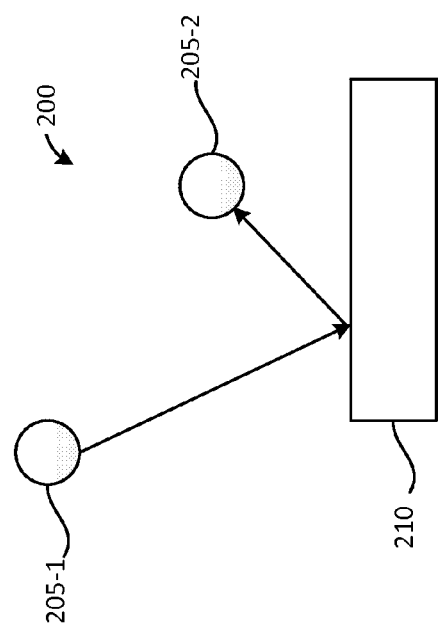

FIGS. 2A-2D illustrate generating acoustic waves when an object is dispensed, dropped, projected, launched, and the like on concrete according to at least one example embodiment. As shown in FIGS. 2A and 2B, an object 205-1, 225-1 is projected toward concrete 210, 230. In system 200, the concrete 210 does not include a defect. In system 220, concrete 230 includes a defect 240. A defect (e.g., defect 240) may be any defect causing an acoustic impedance discontinuity. An acoustic impedance discontinuity may cause a reflection of acoustic energy. For example a defect may be a delamination, a vertical/horizontal/any orientation crack, a bond disjoint/disbondment, and/or the like. The object 205-1, 225-1 contacts the concrete 210, 230 and subsequently bounces or reflects away from the concrete 210, 230 (illustrated as objects 205-2, 225-2). The angle of the objects 205-1, 225-1, 205-2, 225-2 in relation to the concrete 210, 230 may be any angle and may be different angles. For example, the angle of approach and departure may be the same (or substantially the same) for concrete without a defect (e.g., concrete 210). For example, the angle of approach and departure may be the different (or substantially different) for concrete with a defect (e.g., concrete 230).

Figure 2C:
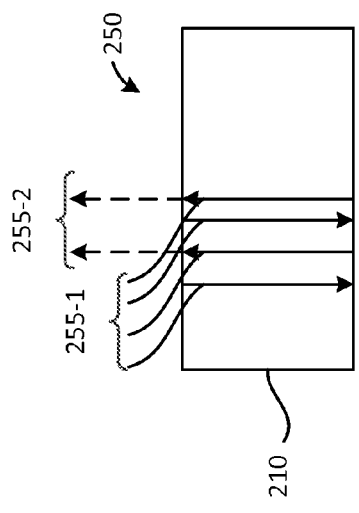

As shown in FIGS. 2C and 2D, waves are generated as a result of the object 205-1, 225-1 coming in contact with concrete 210, 230. Internal waves 255-1, 265, 270-1 bounce or reflect within the concrete 210, 230. The waves have varying wavelengths in the time domain or center frequencies (or contours) in the frequency domain, and varying power (e.g., decibels (dB)), based on the bounces or reflections. For example, the waves that reach the bottom surface of the concrete 210, 230 (e.g., waves 255-1 and 265) have a longer wavelength than those that reflect from a defect 240 (e.g., 270-1). Accordingly, acoustic waves 255-2, 270-2, external to the concrete 210, 230 have wavelengths or frequencies that differ based on the existence of a defect. Acoustic waves 255-2, 270-2 can also be referred to as guided recursive waves or Lamb waves because the concrete can act like a vibrating membrane (or plate) thus generating an acoustic wave based on the vibration. The concrete (as a vibrating membrane) can vibrate differently (e.g., at a different frequency) based on whether or not a defect exists.

A model of solid-solid impacts may be used to describe the force-time characteristics of an impact event. In an example implementation that involves the use of gravity for acceleration of the object 205-1, 225-1 over short or relatively short distances, the object velocity may be limited to, for example, less than 7 m/s. Hertzian contact theory can be applied to such low-velocity, solid-solid impacts. Equations 1-3 below are derived from Hertzian contact theory.

If the collision is perfectly elastic, then the total contact time will be $2t_c$. The maximum force ($F_c$) in terms of the object material properties, velocity, and radius and the concrete properties can be expressed as:

$$F_c = 3.025[(1-v_B)^2 E_B^{-1} + (1-v_{B'})^2 E_{B'}^{-1}]^{-2/5} R_*^2 \sigma_B^{3/5} v_o^{6/5} \quad (1)$$

Where $\sigma_B$ is the density of the object 205-1, 225-1. Where $E_B$ and $v_B$ are the elastic modulus and Poisson's ratio of the object 205-1, 225-1 and $E_{B'}$ and $v_{B'}$ are the elastic modulus and Poisson's ratio of the concrete 210, 230. Where $R_*$ is the effective radius of the object 205-1, 225-1 and concrete 210, 230, which in this case is just the radius of the object 205-1, 225-1 because the concrete 210, 230 is effectively infinite. Where $m_B$ is the mass of the object 205-1, 225-1 and $v_o$ is the velocity of the object 205-1, 225-1 at the time of impact. Equation 1 shows that, if the object material and the concrete have different elastic moduli, the mechanical properties of the material with the smaller elastic modulus will dominate the maximum force. Therefore, in the case of steel-concrete impacts, where steel has an elastic modulus of, for example, 200 GPa and concrete has an elastic modulus of, for example, 30 GPa, the concrete properties will more strongly influence the peak force for a given impact. In the case of ice-concrete impacts, although the difference in elastic moduli between the two materials is comparatively smaller, the properties of the ice will dominate the peak force. For an object with a given radius, the equation also demonstrates that a denser object, such as steel (7850 kg/m3), will also produce a much stronger peak force than a less dense object, such as ice (920 kg/m3). Increasing the velocity of the object when dispensed is advantageous in all cases for increasing the force.

The contact time can also be found from algebraically manipulating and rearranging the previous expression into the expression:

$$t_c = 2.538[(1-v_B)^2 E_B^{-1} + (1-v_{B'})^2 E_{B'}^{-1}]^{2/5} R_* \sigma_B^{3/5} v_o^{-1/5} \quad (2)$$

This expression shows that reducing the effective elastic modulus of the combined system, reducing the impact velocity, or increasing the size or the density of the object 205-1, 225-1 will increase the contact time. The contact time is considered for the type of impact pulse applied to the concrete because it specifies the range of frequencies that will be excited. The development followed here additionally considers that the force-time curve of the linearly approximated Hertzian impact can be characterized as:

$$F(t) = F_c \sin\left(\frac{\pi t}{2t_c}\right) \quad (3)$$

Once the object 205-1, 225-1 has impacted the concrete 210, 230, various transfers of energy occur. Most of the energy is not returned as part of the acoustic response but is dissipated into the concrete 210, 230. In addition, some energy is absorbed through deformation of the object 205-1, 225-1, which, in the case of an ice ball, may even crack. During impact, the concrete 210, 230 is indented, and various waves emanate from the impact point. The high-frequency waves associated with pressure waves being reflected off the bottom of the concrete or embedded defects (e.g., delamination defects) may be, for example, zero-group-velocity Lamb waves that radiate acoustic energy into the air. In addition to the Lamb waves, low-frequency flexural modes representing the plate vibrations of the concrete 210, 230 may be excited.

Figure 3:
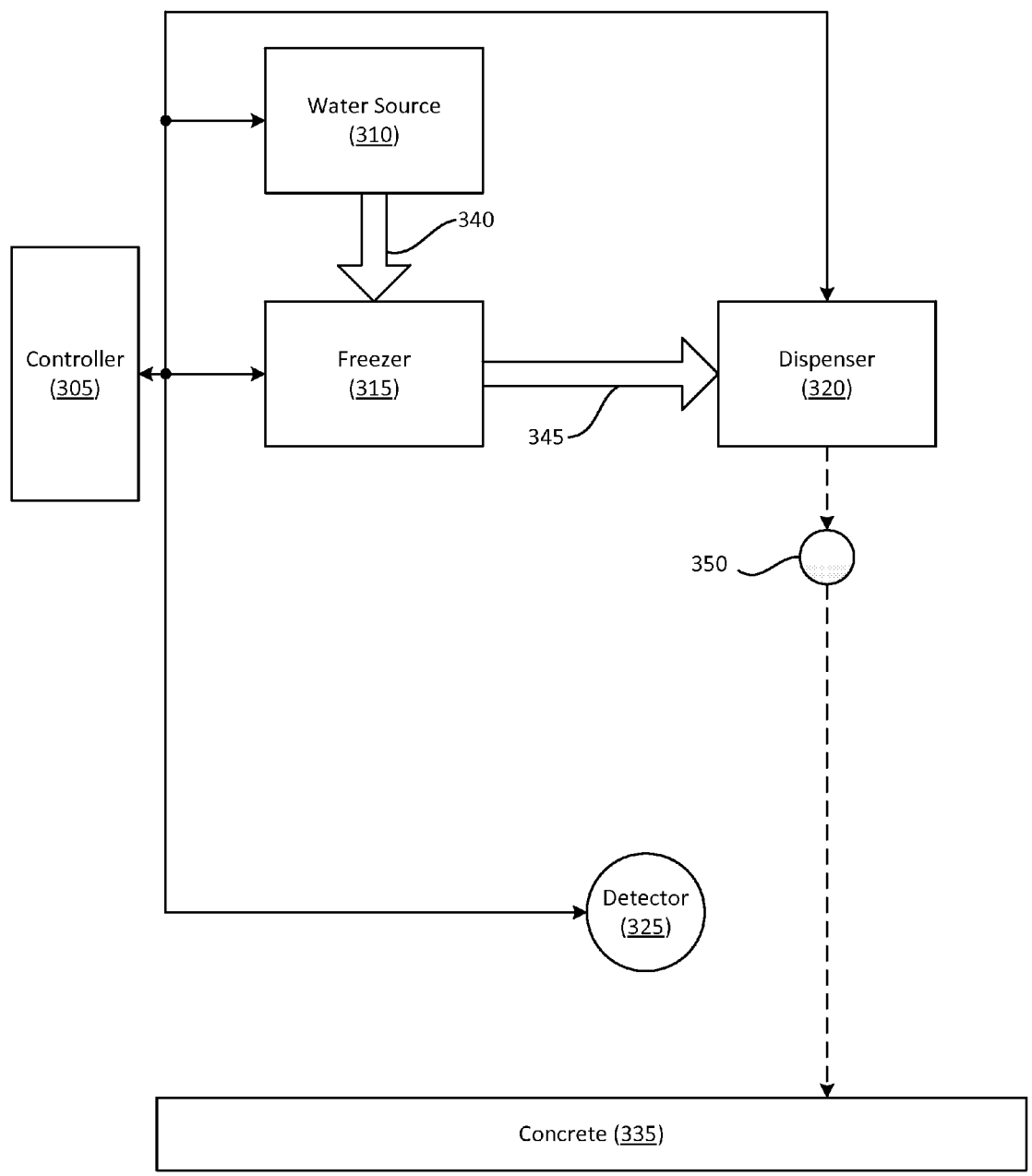

FIGS. 3-5A illustrate block diagrams of systems for detecting a defect in concrete according to at least one example embodiment. As shown in FIG. 3, system 300 includes a controller 305, a water source 310, a freezer 315, a dispenser 320 and a detector 325. The water source 310 and the freezer 315 are coupled by a water conduit 340 (e.g., a hose). The freezer 315 and the dispenser 320 are coupled by an ice conduit 345 (e.g., an auger). The water source 310 may be a water storage tank configured to store water (e.g., potable water). The water source 310 may be an unlimited (or substantially unlimited) water source (e.g., a community water system). The freezer 315 may be configured to generate an ice shape as an object 350 by freezing the water. The shape may be a circle, sphere, triangle, cube, and the like.

The dispenser 320 may be configured to project (or otherwise dispense) the object 350 toward the concrete 335. For example, the dispenser 320 may be configured to drop the object such that gravitational forces project the object 350 toward the concrete 335. For example, the dispenser 320 may use compressed gas, a spring, and/or other mechanism to project (e.g., at a set speed or velocity) the object 350 toward the concrete 335. The detector 325 may be a microphone and a recorder.

Figure 4:
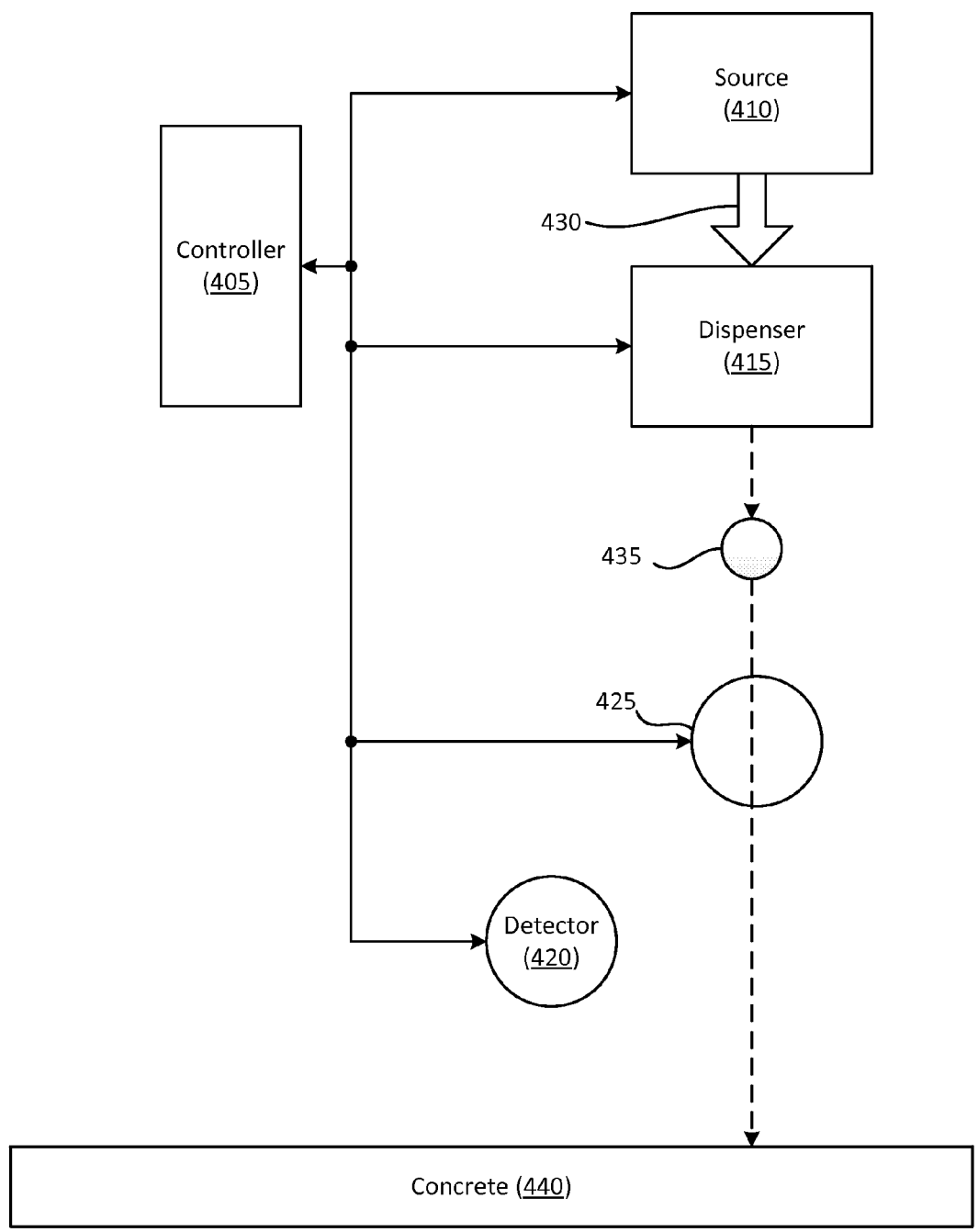

As shown in FIG. 4, system 400 includes a controller 405, a source 410, a dispenser 415, a detector 420 and a sensor 425. The source 410 and the dispenser 415 are coupled by a conduit 430 (e.g., an auger, a hose, a passage, and the like). The conduit 430 may be configured to direct and object 435 to the dispenser 415. For example, the dispenser 415 may be a compressed gas dispenser (e.g., an air gun) and the source 410 may be a spring assisted feeder (e.g., a magazine). Accordingly, the conduit 430 may be the mechanism by which the magazine feeds the air gun.

The dispenser 415 may be configured to project the object 435 toward the concrete 440. For example, the dispenser 415 may be configured to drop the object 435 such that gravitational forces project the object 435 toward the concrete 440. For example, the dispenser 415 may use compressed gas and/or a spring to project (e.g., at a set speed or velocity) the object 435 toward the concrete 440. Accordingly, the dispenser 415 can be a compressed-gas dispenser or can be a spring-based dispenser. The detector 420 may be, for example, a microphone (and a recorder). The sensor 425 may be an infrared (IR) sensor.

In one example implementation, the dispenser 415 can be a compressed-gas dispenser or air gun that launches or shoots a pellet or ball (e.g., biodegradable plastic ball) as the object 435. In this example implementation, the object 435 is projected or launched at a velocity of 100-400 ft/sec. The object may have a mass of, for example, about 0.20 grams to 0.25 grams and a diameter of, for example, about 5 mm to 8 mm.

Figure 5A:
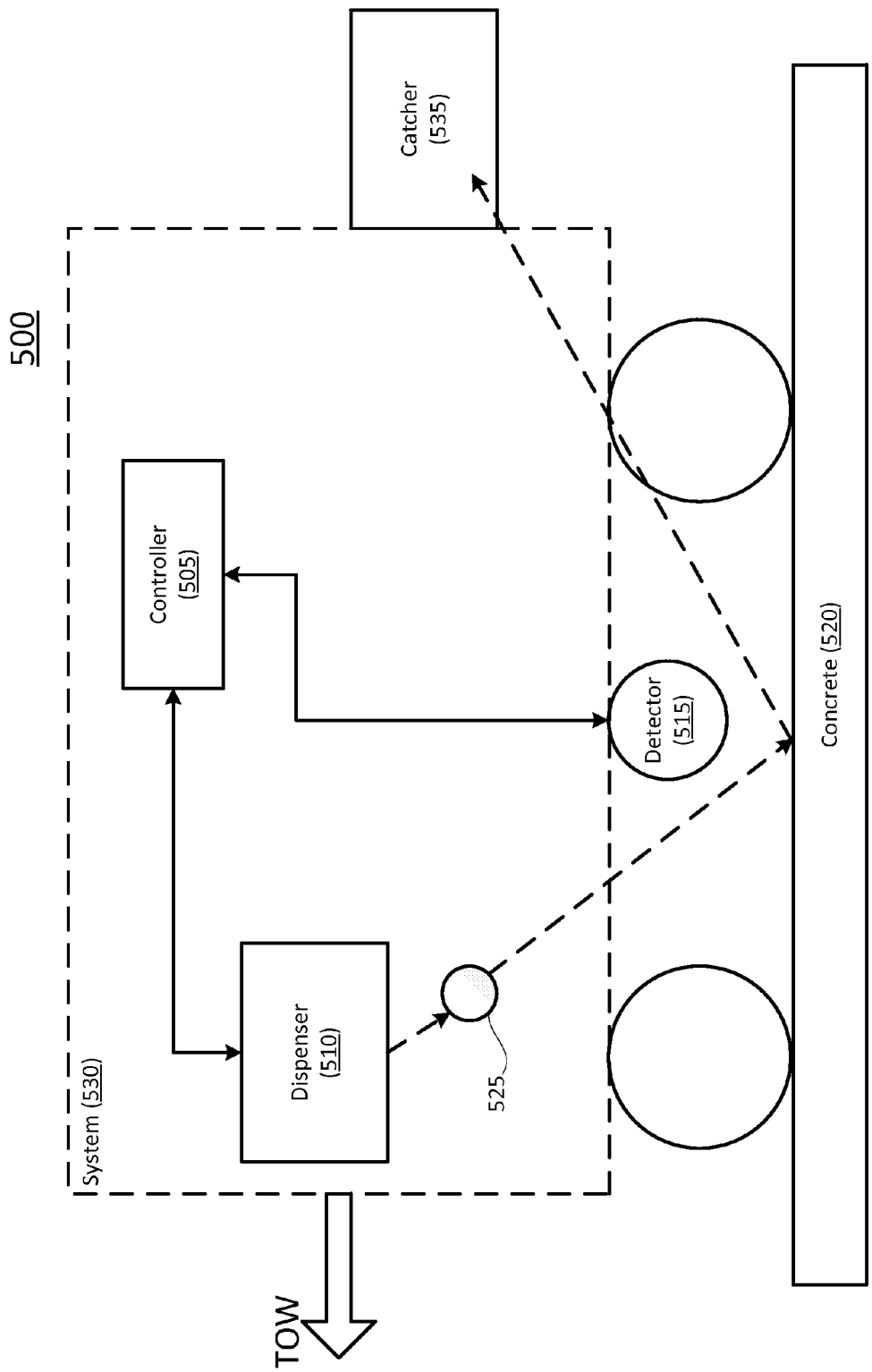

As shown in FIG. 5A, system 500 includes system 530 including a controller 505, a dispenser 510, a detector 515 (e.g., a microphone and a recorder) and a catcher 535 (e.g., a box positioned to catch objects following impact). The catcher 535 may be configured to retrieve at least one object projected by the dispenser 510. The system 530 may be configured to travel along concrete 520 and project an object 525 toward concrete 520 such that a plurality of objects (including object 525) impact on concrete 520 at regular (or substantially regular) intervals (e.g., time or distance intervals). In other words, as the system 530 travels along concrete 520, the dispenser 510 may dispense a plurality of objects and detect (e.g., measure acoustic signals) impacts of each of the plurality of objects. The system 530 may be pulled or towed behind a motorized or non-motorized vehicle (e.g., automobile, wagon, cart). Alternatively, and/or in addition, system 530 may be contained within or may be a motorized or non-motorized vehicle.

As discussed in more detail below with regard to FIG. 6, the controller 505 may be configured to correspond to measurements associated with detector 515 with the impacts. Accordingly, impacts and their corresponding measurements (e.g., acoustic signals can be associated with a location along the concrete 520. In this way, a defect (e.g., a delamination defect) can be detected and associated with a location on the concrete 520. For example, referring to FIG. 5B, as the system 530 travels along concrete in the indicated direction of travel, at time T0, T1, T2, T3, T4, T5 and so on an object 525 can be dispensed by dispenser 510 and a corresponding impact with the concrete 520 detected (and measured) by detector 515.

Although system 530 is shown as including the controller 505, the dispenser 510 and the detector 515, the system 530 may be configured with additional elements as shown in FIG. 3 and/or FIG. 4.

Figure 6:
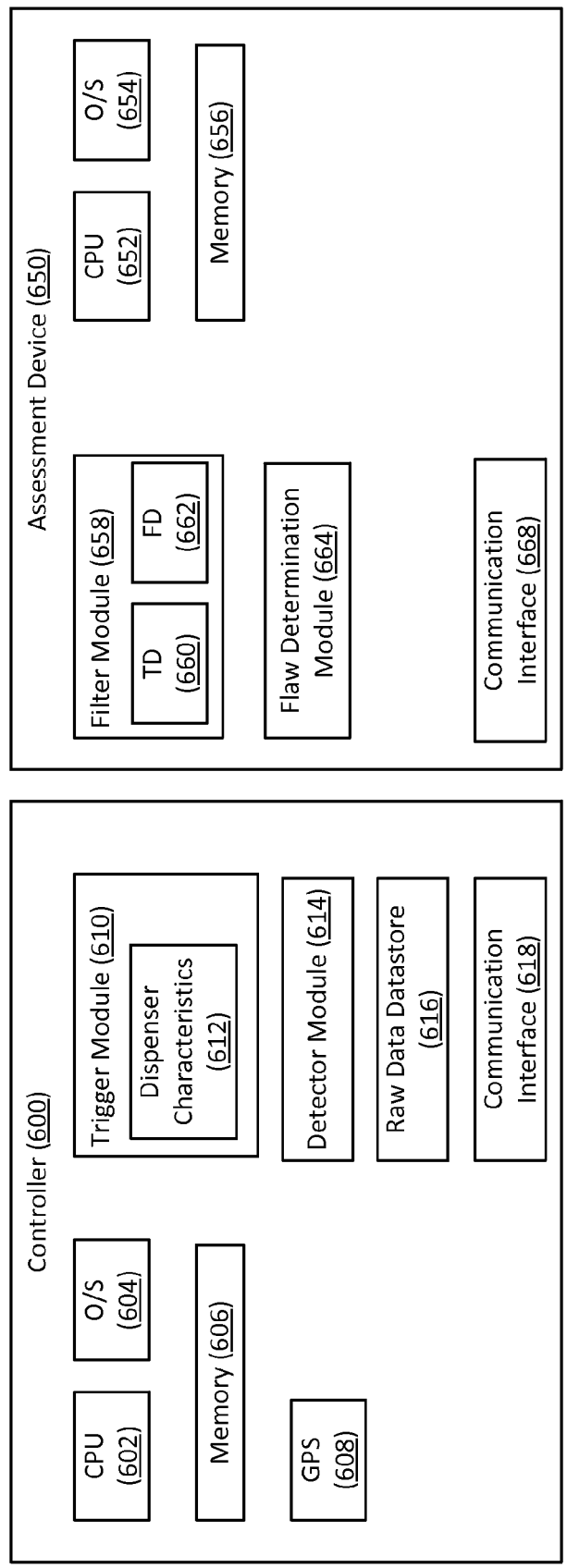
FIG. 6 illustrates a block diagram of a controller and of an assessment device according to at least one example embodiment.

FIG. 6 illustrates a block diagram of a controller and of an assessment device according to at least one example embodiment. As shown in FIG. 6, the controller 600 includes a (or at least one) processor 602, an operating system 604, a (or at least one) memory 606, a global positioning system 608, a trigger module 610 including dispenser characteristics 612, a detector module 614, a raw data datastore 616, and a communication interface 618. As shown in FIG. 6, the assessment device 650 includes a (or at least one) processor 652, an operating system 654, a (or at least one) memory 656, a filter module 658 including a time domain module 660 and a frequency domain module 662, a flaw determination module, and a communication interface 618. In an alternative embodiment, the assessment device 650 is an element or module of the controller 600.

As shown in FIG. 6, the memory 606, 656 includes code that can be executed to provide an operating system (O/S) 604, 654, and at least one associated module. The operating system (O/S) 604, 654, and the at least one associated module (together) may be configured to implement (at least a portion of) the methods described herein. According to example implementations, the operating system (O/S) 604, 654 manages hardware resources associated with the controller 600 and/or the assessment device 650 and provides common services for computer programs executing on the controller 600 and/or the assessment device 650.

The trigger module 610 may be configured to determine an object has been dispensed. In addition, the trigger module 610 may be configured to determine object impact times. Object impact times may be based on when an object is about to, is in the process of and/or has impacted on concrete. In one example embodiment the trigger module 610 calculates associated impact times. Accordingly, the dispenser characteristics 612 may include variable values associated with the dispenser. For example, the variables values may include values associated with a dispense velocity, a distance to the concrete, a dispense angle, characteristics of the object and the like. The variables values may also be associated with characteristics of the object and/or the concrete. For example the variable values may include a shape of the object, a weight of the object, a size of the object, thickness of the concrete, and the like. For example, the variables values may include values associated with equations 1-9 above. Accordingly, the trigger module 610 may be configured to calculate associated impact times based on the dispenser characteristic values and/or the object characteristic values.

In another example embodiment, at least one sensor (e.g., sensor 425) may be configured to indicate the object is about to impact the concrete. For example, the trigger module 610 may receive an indication from the at least one sensor that an object tripped or triggered the sensor (e.g., the object has passed through an IR beam or an audio sensor indicates an object has been dispensed). Accordingly, the trigger module 610 may be configured to calculate associated impact times based on the indication that the object is about to impact the concrete. In yet another example embodiment, the trigger module 610 may be configured to calculate associated impact times based on the indication that the object is about to impact the concrete, the dispenser characteristic values and/or the object characteristic values. In yet another example embodiment, the dispenser may communicate a signal that an object has been dispensed.

The detector module 614 may be configured to read and/or receive measurements from a detector (e.g., detector 115, 325, 420, and/or 515). The measurements may be associated with an object impacting concrete. The measurements may be acoustic waves. The measurements may indicate a defect (e.g., a delamination defect) in the concrete. The measurements may be stored in the raw data datastore 616. The measurements may be stored in the raw data datastore 616 together with information about the measurement (e.g., location and time). The measurements may be stored in correspondence with the associated impact times for an object. The global positioning system (GPS) 608 may be configured to indicate a location of the system including the controller 600 (e.g., system 100, 300, 400 and/or 500). The indication of the location may be stored in correspondence with a measurement in the raw data datastore 616. In other words, the measurement for an acoustic wave associated with an impact may be stored, in the raw data datastore 616, with a corresponding location indicated by the GPS 608.

The flaw determination module 664 may be configured to determine a defect (e.g., a delamination defect) exists (or likely exists) in the concrete. The flaw determination module 664 may determine a defect exists based on the measurements (e.g., acoustic wave measurements). Accordingly, the flaw determination module 664 may be configured to read the measurements stored in the raw data datastore 616. Then the flaw determination module 664 may determine associations between acoustic wave measurements, object impact times and impact locations (e.g., GPS positions).

The filter module 658 may be configured to filter (or remove) undesirable acoustic wave measurements. For each acoustic wave associated with an impact, acoustic waves representing noise or ambient noise (e.g., environmental sounds associated with nearby vehicles) or other undesirable sounds (e.g., spring or air gun shots associated with a dispenser) may be filtered from the acoustic wave measurements. For example, a time domain band reject filter having a window (e.g., a Hamming window) that excludes acoustic waves representing dispenser (e.g., dispenser 110, 320, 415, and/or 510) projection of an object may be used. For example, a time domain band pass filter having a window that passes acoustic waves representing an impact of an object on concrete may be used. Accordingly, the filter module 658 includes a time domain module 660. In another example embodiment the filter module 658 may be configured to detect an acoustic wave signature. For example, a first filter based on an expected wave for no defect may be developed and applied. For example, a second filter based on an expected wave for defect may be developed and applied. The output from applying the first or second filter may indicate whether or not a defect exists in the concrete.

Further, the acoustic waves representing an impact of an object on concrete may be filtered in the frequency domain to filter or remove acoustic waves representing ambient noise. For example, the acoustic waves (e.g., time domain filtered acoustic waves) representing an impact of an object on concrete may be converted (e.g., using a Fourier transform) to the frequency domain as, for example, contours having a center frequency based on the wavelength of the acoustic wave in the time domain. The frequency domain contours may be filtered to remove acoustic waves representing ambient noise. The frequency domain filter may remove contours having a center frequency below a set value. Accordingly, the filter module 658 includes a frequency domain module 662. Although the above description describes the time domain filtering occurring before the frequency domain filtering, in example embodiments the frequency domain filtering may be performed before the time domain filtering. Further, time domain and/or frequency domain filtering may be performed without the other type of filtering.

The flaw determination module 664 may be configured to determine a defect (e.g., a delamination defect) exists (or likely exists) in the concrete based on at least one of the frequency domain or time domain filtered acoustic wave measurement(s). For example, frequency domain contour center frequencies may indicate the difference between concrete with a defect and concrete without a defect. Therefore, in one example embodiment, frequency domain contour center frequencies with values above a first threshold value may be determined as concrete with a defect, and frequency domain contour center frequencies with values below the first threshold value may be determined as concrete without a defect. In another example embodiment, frequency domain contour center frequencies with values below a second threshold value may be determined as concrete with a defect, and frequency domain contour center frequencies with values above the second threshold value may be determined as concrete without a defect. In yet another example embodiment, frequency domain contour center frequencies with values between a third threshold value and a fourth threshold value may be determined as concrete with a defect, and frequency domain contour center frequencies with values not between the third threshold value and the fourth threshold value may be determined as concrete without a defect.

The communication interface 618 and communication interface 668 may be configured to provide a communication channel between the controller 600, the assessment device 650 and/or other computing devices (not shown). The communication channel may be wired or wireless. Accordingly, the communication interface 618 and communication interface 668 may be wired and/or wireless. In other words, the communication interface 618 and communication interface 668 may use at least one wired and/or wireless communications protocol.

Figure 7:
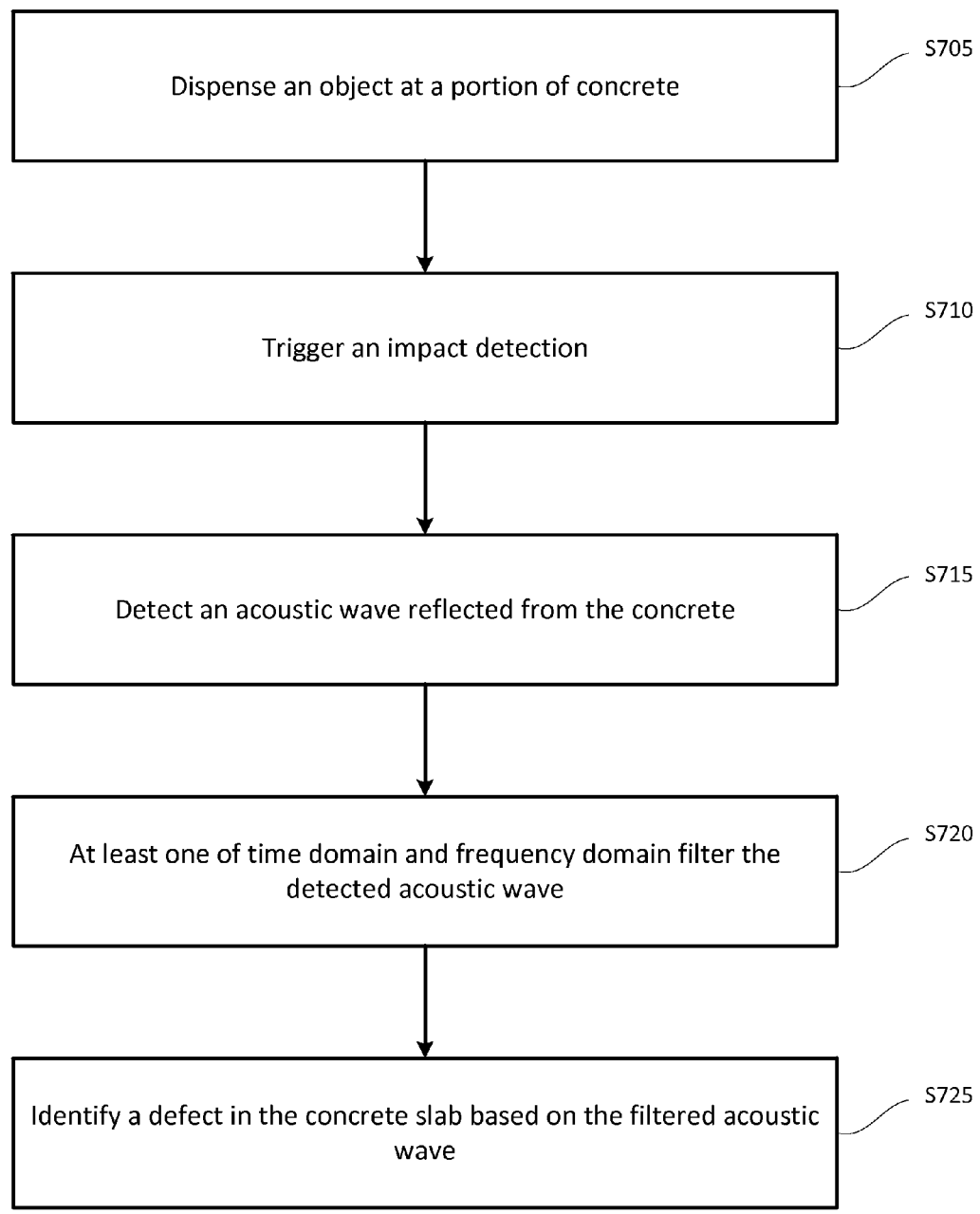
FIG. 7 illustrates a flowchart for detecting a defect in concrete according to at least one example embodiment.

FIG. 7 illustrates a flowchart for detecting a defect in concrete according to at least one example embodiment. The steps described with regard to FIG. 7 may be performed due to the execution of software code stored in a memory (e.g., memory 606 and/or 656) associated with an apparatus (e.g., as shown in FIGS. 1, 3, 4, 5A and 6) and executed by at least one processor (e.g., processor 602 and/or 652) associated with the apparatus. However, alternative embodiments are contemplated such as a system embodied as a special purpose processor. Although the steps described below are described as being executed by a processor, the steps are not necessarily executed by a same processor. In other words, at least one processor may execute the steps described below with regard to FIG. 7.

As shown in FIG. 7, in step S705 an object is projected at a portion of concrete. For example, a dispenser (e.g., dispenser 110, 320, 415 and/or 510) can project (or drops, propels or launches) an object toward a portion of concrete (e.g., concrete 120, 335, 440, 520). As discussed above, projecting an object can include dropping the object or applying a force (e.g., spring or gas acceleration) to the object.

In step S710 impact detection is triggered. For example, triggering impact detection can be based on determining an expected impact time and/or sensing that an impact is about to occur. As discussed above, the trigger module 610 may be configured to calculate associated impact times based on the indication that the object is about to impact the concrete, the dispenser characteristic values and/or the object characteristic values.

In step S715 an object acoustic wave reflected from the concrete is detected. For example, a detector (e.g., detector 115, 325, 420, 515) can measure at least one acoustic wave associated with an impact of the object.

In step S720 at least one of a time domain and a frequency domain filter is applied to the detected acoustic wave. For example, an acoustic wave associated with the impact can include at least one acoustic wave representing ambient noise (e.g., environmental sounds associated with nearby vehicles) or other undesirable sounds (e.g., spring or air gun shots associated with a dispenser) which may be filtered or removed from the acoustic wave measurements. Accordingly, the detected acoustic wave can be filtered in the time domain and/or transformed to the frequency domain and filtered.

In step S725 whether or not a defect (e.g., delamination defect) exists in the concrete slab is determined based on the filtered acoustic wave. For example, as discussed above, a frequency domain contour center frequency may indicate the difference between concrete with a defect and concrete without a defect. Accordingly, a defect may be indicated based on one or more threshold values associated with the frequency domain contour center frequency.

Figure 8A:
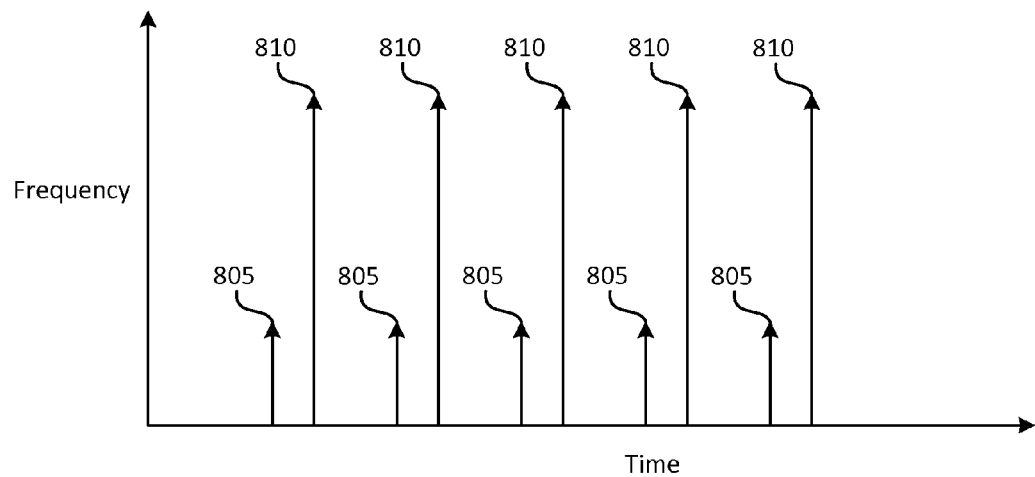
FIGS. 8A-8D illustrate graphs of time vs. frequency contours according to at least one example embodiment.
Figure 8B:
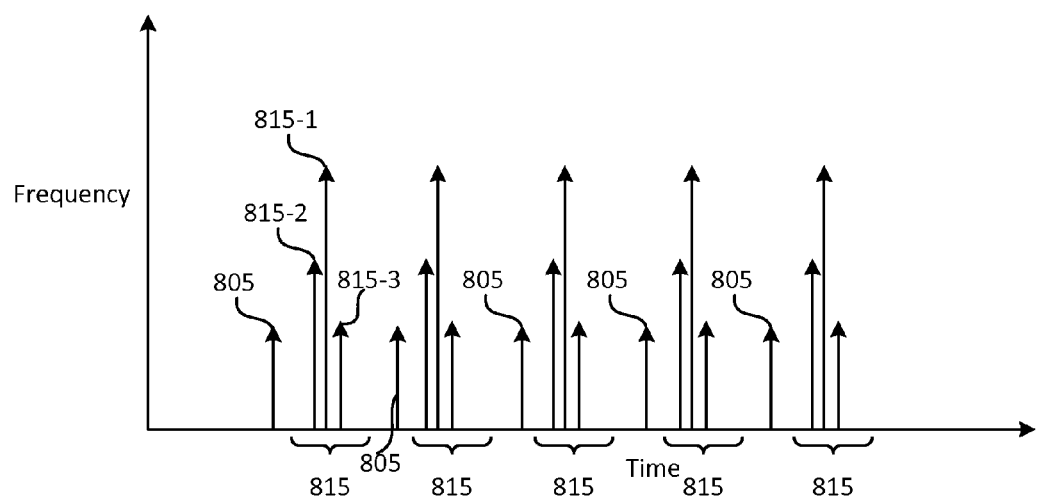

FIGS. 8A-8D illustrate graphs of time vs. frequency contours according to at least one example embodiment. As shown in FIGS. 8A and 8B, contours (e.g., frequency domain representations of acoustic reflections) have a center frequency and can occur incrementally (or substantially incrementally) over time. Contours 805 may represent an acoustic wave measurement (e.g., a reflected wave and/or a Lamb wave) associated with dispensing (e.g., dropping, propelling or launching) an object. Contours 810 and 815 may represent an acoustic wave measurement associated with an impact of the object on concrete.

Each contour can be generated (e.g., by controller 600 or assessment device 650 using a Short-time Fourier transform (STFT). STFT is a signal processing method used for analyzing non-stationary signals (e.g., acoustic wave measurements), with statistical characteristics that vary with time. STFT may be used to extract several frames of the signal to be analyzed with a window that moves with time. If the time window is sufficiently narrow (e.g., a limited number of samples, for example 1024), each frame extracted can be viewed as stationary so that a Fourier transform can be used. With the window moving along the time axis, the relation between the variance of frequency and time can be identified (e.g., frequency variations indicating a defect can be identified).

Contour 810 may represent an acoustic wave measurement associated with a portion of concrete without a defect. Contour 815 may represent an acoustic wave measurement associated with a portion of concrete with a defect. Contour 815 may include a plurality of contours including a contour 815-1 having a center frequency similar (somewhat similar, substantially equal to) a center frequency of contour 810. Contour 815 may include a plurality of contours having at least one resonance frequency generated based on a defect.

Figure 8C:
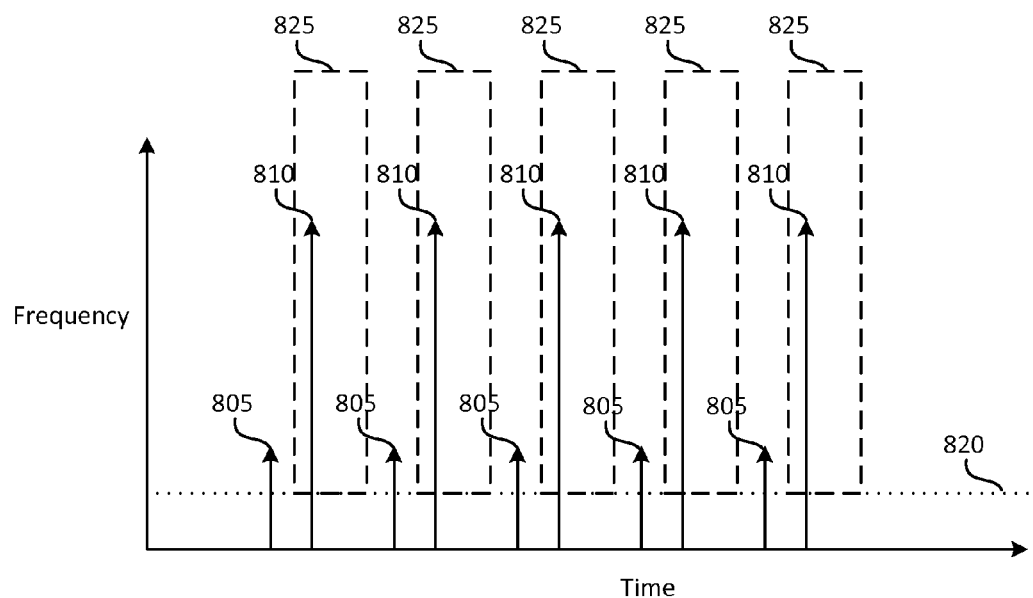
Figure 8D:
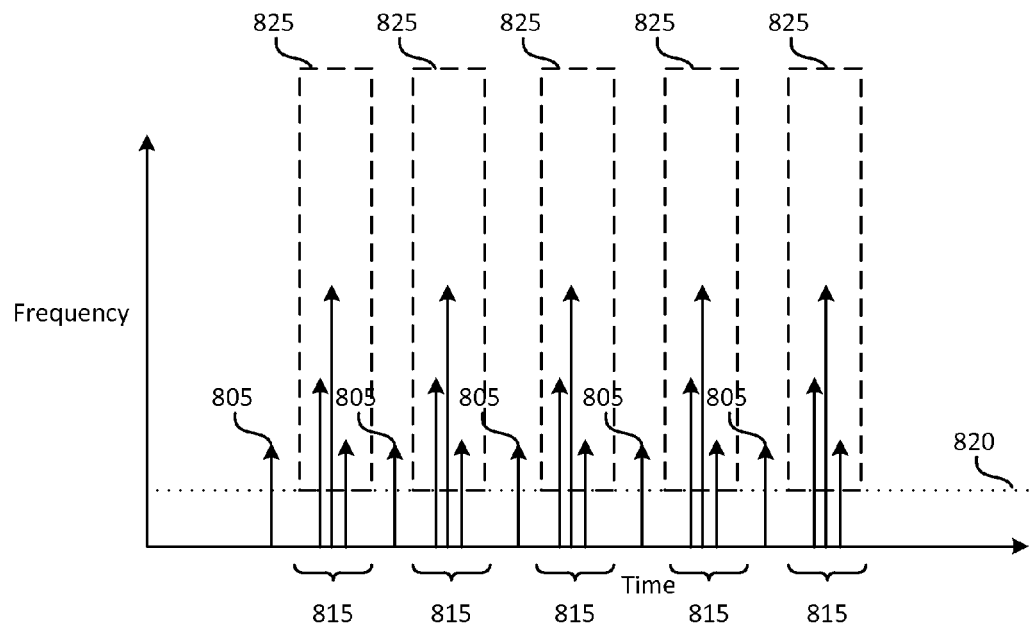

As shown in FIGS. 8C and 8D, a filter window 825 (e.g., as applied by filter module 658) filters or removes the contour 805 that represents the acoustic wave measurement associated with dispensing (e.g., dropping, propelling or launching) the object. The filter window 825 also filters or removes noise or ambient noise 820. The filter window 825 may also vary with time, isolating a number of impacts over time. For example, each filter window 825 may represent one impact in a STFT. The filter window 825 may be implemented in the time domain and/or the frequency domain. For example, the filter window 825 may be implemented in two steps. In a first step, a time domain filter may remove the contour 805. In a second step, a frequency domain filter may remove the noise or ambient noise 820.

According to an example implementation based on the steps described with regard to FIG. 7 and windowing described with regard to FIGS. 8C and 8D, the dispensing of the object can include dispensing a first object at a first time, and dispensing a second object at a second time. Then the determining of the impact time of the object may include determining an impact time of the first object and determining an impact time of the second object. The filtering of the at least one acoustic wave may include applying a window that moves with time based on the impact time of the first object and an impact time of the second object, or the window may be configured to isolate an acoustic wave associated with the first object from an acoustic wave associated with the second object. This example implementation may be performed while a system is traveling along a roadway or bridge as described above with regard to FIG. 5A.

Some of the above example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed above, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks may be stored in a machine or computer-readable medium such as a storage medium. A processor(s) may perform the necessary tasks.

Specific structural and functional details disclosed herein are merely representative for purposes of describing example embodiments. Example embodiments, however, may be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the above example embodiments and corresponding detailed description are presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the above illustrative embodiments, reference to acts and symbolic representations of operations (e.g., in the form of flowcharts) that may be implemented as program modules or functional processes include routines, programs, objects, components, data structures, etc., that perform particular tasks or implement particular abstract data types and may be described and/or implemented using existing hardware at existing structural elements. Such existing hardware may include one or more Central Processing Units (CPUs), digital signal processors (DSPs), application-specific-integrated-circuits, field programmable gate arrays (FPGAs) computers or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

Note also that the software implemented aspects of the example embodiments are typically encoded on some form of non-transitory program storage medium or implemented over some type of transmission medium. The program storage medium may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

Lastly, it should also be noted that whilst the accompanying claims set out particular combinations of features described herein, the scope of the present disclosure is not limited to the particular combinations hereafter claimed, but instead extends to encompass any combination of features or embodiments herein disclosed irrespective of whether or not that particular combination has been specifically enumerated in the accompanying claims at this time.

What is claimed is:

1. A method comprising:
dispensing a first object at a first portion of concrete;
dispensing a second object at a second portion of concrete;
determining a first impact time of the first object on the first portion of concrete;
determining a second impact time of the second object on the second portion of concrete;
detecting at least one acoustic wave reflected from the first portion of concrete and the second portion of concrete;
filtering the at least one acoustic wave using a filter window that moves with time based on the first impact time and the second impact time, the filter window being configured to differentiate between an acoustic wave associated with impact of the first object and an acoustic wave associated with impact of the second object; and
identifying a defect in at least one of the first portion of concrete and the second portion of concrete based on the filtering.

2. The method of claim 1, wherein the first object and the second object are one of a plurality of objects each dispensed in succession.

3. The method of claim 1, wherein the portion of concrete is a portion of a roadway or bridge and the first object and the second object are one of a plurality of objects, the method further comprising:
changing a dispense location along the roadway or bridge;
dispensing each of the plurality of objects incrementally along the roadway or bridge; and
identifying an impact location on the roadway or bridge for each of the plurality of objects, the identifying a defect includes identifying if a defect exists at each impact position.

4. The method of claim 1, wherein the dispensing of the first object and the second object are one of a compressed gas launch and spring assisted launch.

5. The method of claim 1, wherein each of the first object and the second object dissipates into an environment surrounding the portion of concrete without a negative impact on the environment surrounding the portion of concrete.

6. The method of claim 1, wherein the filtering of the at least one acoustic wave includes time domain filtering of the at least one acoustic wave associated with the dispensing of the first object and the second object.

7. The method of claim 1, wherein the filtering of the acoustic wave includes,
converting the acoustic wave into the frequency domain, and
frequency domain filtering of ambient noise.

8. The method of claim 1, wherein the identifying of a defect includes,
converting the acoustic wave into the frequency domain,
determining a center frequency of an contour, and
identifying a defect based on the center frequency of the contour and a threshold value.

9. A system comprising:
a dispenser configured to project a first object toward a first portion of concrete and configured to project a second object at a second portion of concrete;
a detector configured to detect at least one acoustic wave, the at least one acoustic wave being reflected from the first portion of concrete in response to impact of the first object and reflected from the second portion of concrete in response to impact of the second object; and
an assessment device configured to:
filter the at least one acoustic wave using a filter window that moves with time, the filter window being configured to differentiate between an acoustic wave associated with the impact of the first object and an acoustic wave associated with the impact of the second object, and
identify a defect based on the results of the filter.

10. The system of claim 9, wherein
the assessment device includes a filter module, and
the filter module is configured to apply at least one of a time domain filter and a frequency domain filter to remove at least one acoustic wave associated with the dispensing of the first object and the second object and at least one acoustic wave associated with ambient noise.

11. The system of claim 9, wherein
the assessment device includes a flaw determination module,
the flaw determination module is configured to convert the at least one acoustic wave reflected from the portion of concrete to a frequency domain as at least one contour having a center frequency, and
the flaw determination module is configured to identify a defect based on the center frequency of the at least one contour and a threshold value.

12. The system of claim 9, further comprising:
a vehicle configured to move the system along a roadway or bridge; and
a global positioning system configured to determine a position of the system, wherein
the portion of concrete is a portion of the roadway or bridge and the first object and the second object are one of a plurality of objects,
the dispenser projects each of the plurality of objects incrementally along the roadway or bridge, and
the assessment device identifies an impact position on the roadway or bridge for each of the plurality of objects and identifies whether or not a defect exists at each impact position.

13. The system of claim 9, further comprising a datastore configured to store a plurality of measurements associated with the at least one acoustic wave in correspondence with associated impact times for the first object and the second object and a location of the impact of the object.

14. The system of claim 9, wherein the assessment device filters the at least one acoustic wave using at least one of a time domain filter and a frequency domain filter.

15. The system of claim 9, wherein the assessment device,
removes at least one acoustic wave associated with a dispensing of the first object and the second object using a time domain filter; and
removes at least one acoustic wave associated with ambient noise using a frequency domain filter.

16. The system of claim 9, further comprising a catcher configured to retrieve at least one object projected by the dispenser.

17. A non-transitory computer readable medium including code segments that, when executed by a processor, cause the processor to:
process a plurality of records from a datastore, the plurality of records including at least one measurement associated with an acoustic wave reflected from a portion of concrete upon impact of an object and information about the measurement;
filter the at least one measurement using at least one of a time domain filter and a frequency domain filter, each of the time domain filter and the frequency domain filter include a filter window that moves with time, the filter window being configured to differentiate between an acoustic wave associated with an impact of a first object on the portion of concrete at a first location and an acoustic wave associated with an impact of a second object on the portion of concrete at a second location; and
identify a defect in the portion of concrete based on the filtered at least one measurement.

18. The computer readable medium of claim 17, wherein the code segments further cause the processor to:
convert the at least one measurement to a frequency domain as at least one contour having a center frequency; and
to identify a defect based on the center frequency of the at least one contour and a threshold value.

19. The computer readable medium of claim 17, wherein the filtering of the at least one measurement includes,
removing at least one measurement of an acoustic wave associated with a dispensing of the first object and the second object using the time domain filter; and
removing at least one measurement of an acoustic wave associated with ambient noise using the frequency domain filter.

* * * * *